United States Patent [19]
Elsasser

[11] Patent Number: 5,874,625
[45] Date of Patent: Feb. 23, 1999

[54] PROCESS TO HYDROGENATE ORGANIC NITRILES TO PRIMARY AMINES

[75] Inventor: A. Fred Elsasser, Cincinnati, Ohio

[73] Assignee: Henkel Corporation, Plymouth Meeting, Pa.

[21] Appl. No.: 743,263

[22] Filed: Nov. 4, 1996

[51] Int. Cl.$^6$ .................................................. C07C 209/48
[52] U.S. Cl. .................... 564/490; 564/415; 564/448; 564/491; 564/492; 564/493
[58] Field of Search ..................... 564/485, 415, 564/448, 490, 491, 492, 493

[56] References Cited

U.S. PATENT DOCUMENTS

| | | | |
|---|---|---|---|
| 2,287,219 | 3/1942 | Young et al. | 260/583 |
| 2,449,036 | 9/1948 | Grunfeld | 260/583 |
| 2,793,219 | 5/1957 | Barrett et al. | 260/448 |
| 2,955,121 | 10/1960 | Myers et al. | 260/407 |
| 3,372,195 | 3/1968 | Little | 260/570.7 |
| 3,565,957 | 2/1971 | Mirviss et al. | 260/583 |
| 3,998,881 | 12/1976 | Butte, Jr. et al. | 260/563 |
| 4,186,146 | 1/1980 | Butte, Jr. et al. | 260/570.5 |
| 4,235,821 | 11/1980 | Butte, Jr. et al. | 564/491 |
| 4,248,799 | 2/1981 | Drake | 564/491 |
| 4,739,120 | 4/1988 | Zuckerman | 564/385 |
| 4,885,391 | 12/1989 | Herkes | 564/491 |
| 5,034,560 | 7/1991 | Cesa et al. | 564/493 |

OTHER PUBLICATIONS

Bailey's Industrial Oil and Fat Products, vol. 1, Fourth Edition, ed. Daniel Swern, John Wiley & Sons, NY, 1979. References to "tall oil": pp. 729–730.
Bailey's Industrial Oil and Fat Products, vol. 2, Fourth Edition, ed. Daniel Swern, John Wiley & Sons, NY, 1982. References to "tall oil": p. 384, p. 390.

*Primary Examiner*—Brian M. Burn
*Attorney, Agent, or Firm*—Ernest G. Szoke; Wayne C. Jaeschke; Martin G. Meder

[57] ABSTRACT

An improved, optimized industrial process has been found for the hydrogenation of organic nitrites into primary amines, which essentially consists of contacting a dried charge of at least one organic nitrile, aqueous alkali metal hydroxide, at least one Raney slurry hydrogenation catalyst, water and hydrogen for an effective time and at an effective temperature and pressure, wherein the improvements comprise eliminating the steps of drying the charge and adding water and reducing the required water to about 0.2%. Secondary and tertiary amine formation is low, as is moisture content and neither precious metals such as rhodium, nor strategic metals, such as cobalt nor ammonia gas nor solvents are required. Surprisingly, it has been found that water levels less than that taught in the prior art are effective at suppressing secondary and tertiary amine production, while still producing repeatable product on an industrial scale and with reduced cycle time, energy and catalyst charge.

19 Claims, No Drawings

PROCESS TO HYDROGENATE ORGANIC NITRILES TO PRIMARY AMINES

FIELD OF THE INVENTION

This invention relates to hydrogenation and more particularly, to the hydrogenation of organic nitrites into primary amines

BACKGROUND OF THE INVENTION

Hydrogenation of organic nitriles to primary amines, as aminomethyl groups, can be accomplished via the use of a Raney sponge nickel or cobalt aqueous slurry catalyst or precious metal catalysts. The nitrile and catalyst are charged into a stirred autoclave, oxygen is removed by reducing pressure or applying heat or both or by sparging with hydrogen or an inert gas, the autoclave is pressurized with hydrogen and heated to temperature. After completion of the reaction the primary amine is separated from the slurry catalyst by decantation or filtration. Fixed bed reactors have been used in an analogous way. Unfortunately, this process, without more, often produces undesirable quantities of secondary and tertiary amines, also known as "heavies." Attempts to reduce the amount of secondary and tertiary amines have generally involved the use of additives to the initial charge. For instance, when 25% nitrile in an ether solvent is hydrogenated in the presence of 5 to 15% water, catalyst and ammonia has been found to yield about 93% primary amine. Consider also, that when an aliphatic dinitrile is hydrogenated in the presence of water, 1 to about 100 wt. % ammonia based on nitrile and catalyst, that the heavies can be as low as 2.3% at maximal ammonia usage. In a different lab, a rhodium catalyst was used in conjunction with water, an alkali metal hydroxide and an immiscible organic solvent such as alkanes, aromatic or alicyclic hydrocarbons to hydrogenate an organic nitrile group. If hydrogen cyanide is not objected to, the cautious investigator may find it of interest that the hydrogenation of acetonitrile to ethylamine in basic aqueous solution may be carried out in its presence. Additionally, Raney cobalt, in combination with 0.5 to 4% water may be used to produce C4 to C12 amines.

Perhaps the prototypical prior art process for the hydrogenation of fatty acid nitrites is as follows: fatty acid nitrile is mixed with 1–2 wt. % water, 0.1 wt. % alkali metal hydroxide, Raney nickel catalyst, sparged with hydrogen to remove dissolved oxygen, and hydrogenated at 200 psi at 140° C. for 110 minutes to yield fatty amine at 78% yield.

In a prior art industrial (ca. 5 mt capacity) autoclave process to produce a primary amine, dimer diamine from an organic nitrile, dimer dinitrile, an autoclave was fed an approx. 4200 kg charge that ultimately comprised dimer dinitrile, about 0.8 wt. % water, about 0.1 wt. % sodium hydroxide (about 16% of catalyst) and about 2 to about 2.4 wt. % Raney nickel. The process comprised the following steps:

1) Charging the organic nitrile to an autoclave.
2) Removing oxygen from the organic nitrile, in this reactor, by heating the dimer nitrile under vacuum and breaking vacuum with an inert gas such as nitrogen.
3) Adding Raney catalyst slurry and aqueous alkali metal hydroxide, about 0.2 wt. % of about 50 wt% sodium hydroxide, under the inert gas blanket.
4) Drying the charge to less than about 0.1 wt. % moisture, in this reactor by pulling a vacuum of at least about 686 mmHg and heating to about 127° C.
5) Cooling the autoclave to below the boiling point of water, about 88° C.
6) Adding water, about 0.77 wt. %, to the charge.
7) Pressurizing with hydrogen, to about 200 to about 400 psi.
8) Heating the converter, to about 160° C.
9) Controlling the reaction exotherm that occurs by, for instance, restricting hydrogen feed and using cooling water.
10) Cooling the resulting amine when the reaction is complete
11) Separating the primary amine from the catalyst, by filtering or decanting, to obtain the desired primary amine product, which may then be optionally distilled.

Total amines yield is greater than 95%. The product specifications are a primary amine value of 185 minimum and a secondary plus tertiary amine value of 15 maximum. The dimer amine typically obtained contains 3–4% moisture and 5% secondary and tertiary amines, for a process yield of about 91% primary amine. The product typically has an amine value of about 191 and a secondary plus tertiary amine value of about 2.5 to 3.5% and a Gardner color of about 9.7.

Note here that water is being added to the initial charge from the sodium hydroxide solution and from the catalyst, as Raney nickel catalyst is shipped as a nickel sponge powder slurry in 50% water to avoid pyrophoric ignition. The water is present as a supernatant fluid which is decanted prior to adding catalyst to the charge. Variability in the settling and compaction of the catalyst leads to some uncertainty as to exactly how much water is being added to the charge, perhaps explaining the current industry practice to dry the charge, to get a consistent baseline, and then to add back a specific amount of water, so as to get repeatability in the process and product. While the percent variability in the water charge may not be high when the water content in the catalyst is low compared to the total added water desired, a high amount of water in the charge is not desirable when low-moisture content product is desired, such as when the product is intended for use in making polyurethanes.

SUMMARY OF THE INVENTION

An improved, optimized industrial process has been found for the hydrogenation of organic nitriles into primary amines, which essentially consists of contacting a dried charge of at least one organic nitrile, aqueous alkali metal hydroxide, at least one Raney slurry hydrogenation catalyst, water and hydrogen for an effective time and at an effective temperature and pressure, wherein the improvements comprise eliminating the steps of drying the charge and adding water and reducing the required water to about 0.2%. Secondary and tertiary amine formation is low, as is moisture content and neither precious metals such as rhodium, nor strategic metals, such as cobalt, nor ammonia gas, nor solvents are required. Surprisingly, it has been found that water levels less than that taught in the prior art are effective at suppressing secondary and tertiary amine production, while still producing repeatable product on an industrial scale and with reduced cycle time, energy and catalyst charge. In one embodiment of the invention, a prior art process for making primary amines from nitriles comprises the steps of charging an organic nitrile to an autoclave, removing oxygen from the organic nitrile, adding Raney catalyst slurry and aqueous alkali metal hydroxide under an inert gas blanket, drying the charge in the autoclave, adding water to the autoclave charge, pressurizing with hydrogen, heating the autoclave toward a final temperature, controlling the reaction exotherm that occurs as the organic nitrile is reduced to a primary amine, cooling the resulting primary amine when the reaction is complete and separating the amine from the catalyst to obtain the desired primary amine product, is improved by eliminating the steps of drying the charge in the autoclave and adding water to the autoclave charge.

In another embodiment, a prior art process for the hydrogenation of organic nitriles into primary amines, which consists of contacting at least one organic nitrile, about 0.1 part alkali metal hydroxide, at least one Raney hydrogenation catalyst, 1 to 2 wt. % water for 110 minutes reaction time at 140° C. and 200 psi hydrogen pressure is improved by decreasing the water to less than 0.6 wt. %, and preferably to between about 0.1 and 0.3 wt. %, and most preferably to about 0.2 wt. %.

DETAILED DESCRIPTION OF THE INVENTION

Based on actual tests, it has been found that repeatable primary amine products may be made on an industrial scale without the necessity of drying the charge to establish a baseline water content level. Unexpectedly, the use of water levels lower than those in general use allows for increased charge size per unit catalyst and reduced energy use while still maintaining acceptably low levels of secondary and tertiary amines.

The primary amines of the present invention have a multiplicity of uses ranging from epoxy and urethane curing agents to polyamide and textile antistat precursors.

The reactor charge of this invention has three major components (other than hydrogen). The first component is an organic nitrile the second component is a Raney hydrogenation catalyst and the third component is aqueous alkali metal hydroxide. The nature of these components will be addressed in turn below. Discussion of the reaction conditions, time, temperature and pressure, follows.

The Organic Nitrile

"Organic nitrile" is defined herein as an organic material containing at least one nitrile, also known as cyano, (—CN) group. The organic material may be an aliphatic-, aromatic-, cycloaliphatic-, heterocyclic-, heteroaliphatic-nitrile, such as alkylene oxides and amines and their cyanoethylated products and the like. Of course, the organic material may have more than one nitrile group, both amine and nitrile groups, and may also be unsaturated. Fatty dimer dinitriles, and unsaturated fatty dimer dinitriles are preferred starting materials, but others that may be used include: acrylonitrile, methacrylonitrile, propionitrile, benzonitrile, 2-methylglutaronitrile, isobutyronitrile, dicyanocyclooctane, nitrilotriacetonitrile, iso- and terephthalonitrile, 1,3,5-tricyanobenzene, o-, m-, or p-tolunitrile, o-, m-, or p-aminobenzonitrile, phthalonitrile, trimesonitrile, 1-naphthonitrile, 2-naphthonitrile, cyclobutanecarbonitrile, cyclopentanecarbonitrile, cyclohexanecarbonitrile, 1,4-cyclohexanedicarbonitrile, 1,2,4,5-cyclohexanetetracarbonitrile, cycloheptanecarbonitrile, 3-methylcycloheptanecarbonitrile, cyclooctanecarbonitrile, butyronitrile, valeronitrile, capronitrile, 2,2-dimethylpropanenitrile, enanthonitrile, caprylnitrile, pelargonitrile, decanenitrile, hendecanenitrile, lauronitrile, tridecanenitrile, myristonitrile, pentadecanenitrile, palmitonitrile, heptadecanenitrile, stearonitrile, phenylacetonitrile, malononitrile, succinonitrile, glutaronitrile, adiponitrile, 1,3,5-tricyanopentane, 4-methyl-3-hexenedinitrile, 4-ethyl-3-hexenedinitrile, 5-methyl-4-nonenedinitrile, 5-ethyl4-decenedinitrile, 7-methyl-6-tridecenedinitrile, 7-methyl -6-pentadecened initrile, 12-methyl-1 2-tetracosenedinitrile, 10-hexyl-9-tetracosenedinitrile, 2,3-dimethyl-3-hexenedi nitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8, 10-tetrapropyl-3-dodecenedinitrile, 2,4,7,9,11,13,15-heptaethyl-6-hexadecenedinitrile, 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedi nitrile, 2-methyl-7-ethyl-4-methyleneoctanedinitrile, 2,4, 8-tri methyl-6-methylenedodecanedinitrile 2,4,8,10-tetrapropyl-6-methylenedodecanedinitrile, 2,26-dimethyl-14-methyleneheptacosanedinitrile, aminoacetonitrile, hexamethylene-1,6-dinitrile, the cyanoethylated derivatives of methanol, ethanol, butanol, pentanol, and the like; from methyl amine, ethyl amine, butyl amine, octyl amine, ethylene glycol, propylene glycol, butylene glycol, propylene glycol, diethylene glycol, dipropylene glycol, hydroquinone, phloroglucinol, 1,4-cyclohexanediol, 1,4-di (hydroxymethyl)cyclohexane, polyethylene glycols, polypropylene glycols, polyoxyalkylene polyethers, polyester polyols, polyol adducts derived from ethylene and/or propylene oxide and methylenedianiline and polyethylene polyphenylamine mixtures, vinyl reinforced polyether polyols, e.g. polyols obtained by the polymerization of styrene or acrylonitrile in the presence of the polyether, polyacetals from glycols such as diethylene glycol and formaldehyde, polycarbonate polyols such as from butanediol and diaryl carbonates, resole polyols, hydroxy terminated polybutadiene resins, ethylene diamine, butylene diamine, polyamines such as primary amine terminated polyether resins and the like, compounds including $C_{12}H_{25}CN$, $NC-(CH_2)_6-CN$, $NC-(CH_2)_{18}-CN$, $CH_3CH_2CH_2-O-CH_2CH_2-CN$, $NC-CH_2CH_2CH_2-O-CH_2CH_2-O-CH_2CH_2-CN$ $NCCH_2CH_2OCH_2CH_2CH_2OCH_2CH_2CN$, $NCCH_2CH_2OCH_2CH(CH_3)OCH_2CH_2CN$, $NCCH_2CH_2O(CH_2)_4OCH_2CH_2CN$, $NCCH_2CH_2OCH_2CH_2CH(CH_3)OCH_2CH_2CN$, $[NCCH_2CH_2OCH(CH_3)-]_2$, $(CH_3)_2C(OCH_2CH_2CN)CH_2OCH_2CH_2CN$, $NCCH_2CH_2O(CH_2)_3CH(CH_3)OCH_2CH_2CN$, $NCCH_2CH_2O(CH_2)_5OCH_2CH_2CN$, $NCCH_2CH_2O(CH_2)_6OCH_2CH_2CN$, $NCCH_2CH_2O(CH_2)_{10}OCH_2CH_2CN$, $NC-CH_2CH_2NH(CH_2)_{12}NHCH_2CH_2-CN$, and 3,3'-(ethylenedioxy)-dipropionitrile $(NC-C_2H_4-O-C_2H_4-O-C_2H_4-CN)$ and mixtures thereof.

Particularly preferred starting organic nitrites are dimer di- and higher- nitrites, known as a class as "dimer dinitriles." They are made by converting dimer acids to nitriles, as is well known in the art, and their molecular weights, functionality, degree of unsaturation and other properties are determined by those of the dimer acids from which they are made. Dimerized fatty acids are also known as polymerized fatty acids, which include aliphatic dicarboxylic acids having from about 32–40 carbon atoms obtained by the polymerization of olefinically unsaturated monocarboxylic acids having from 16–20 carbon atoms, such as palmitoleic acid, oleic acid, linoleic acid, linolenic acid and the like. Polymeric fatty acids and processes for their production are well known. See, for example, U.S. Pat. Nos. 2,793,219 and 2,955,121, both incorporated herein by reference as if set forth in their entirety. Polymeric fatty acids particularly useful in the practice of this invention preferably will have as their principal component C-36 dimer acid. Such C-36 dicarboxylic acids are obtained by the dimerization of two moles of a C-18 unsaturated monocarboxylic acid, such as oleic acid or linoleic acid, or mixtures thereof, e.g., tall oil fatty acids. These products typically contain 75% by weight or more of C-36 dimer acid and have an acid value in the range of 180–215, saponification value in the range of 190–215 and neutral equivalent from 265–310. Examples of commercial dimer acids of this type are EMPOL® 1008, EMPOL® 1015, EMPOL® 1061, EMPOL® 1016, EMPOL® 1018, EMPOL® 1022 and EMPOL® 1024, all trademarked products of the Henkel Corporation. To increase the C-36 dimer content and reduce the amount of by-product acids, including unreacted monobasic acid, trimer and higher polymer acids, the polymeric fatty acid may be molecularly distilled or otherwise fractionated. VERSADYME 288 (TM Henkel Corp.) is a preferred distilled tall oil dimer acid precursor of the dimer dinitrile used as starting material in Examples 1–4 given below. Typical properties are an acid value of 193–201 and a composition that is about 2.5 5 wt. % monobasic, about 92.5–95.5 wt. % dibasic and about 1.5–3.5 wt. % poly (tri- and higher-) basic. It is substantially converted to a dinitrile, #513, prior to use. The dimer acids may be hydrogenated prior to conversion to dinitrile to reduce unsaturation and color. EMPOL® 1061, also known as VERSADYME 52, both trademarked products of the Henkel Corporation, is also used as a starting material to make the dimer dinitrile, #523, of Example 5, and it is a hydrogenated version of Versadyme 288 and it has an iodine value of about 20 maximum.

The Raney Hydrogenation Catalyst

The preferred catalysts are Raney nickel and cobalt slurry catalysts, with or without group VIB metal and manganese and iron promoters, with nickel being more preferred as it will work and is not an expensive, strategic metal like cobalt. These catalysts are generally made by preparing, for example, a 50–50 aluminum-nickel powder and then reacting that powder with aqueous sodium hydroxide solution to leach away most of the aluminum, leaving substantially nickel powder with very high surface area. The high surface area imparts catalytic activity, but it also renders the powder pyrophoric. Therefore, the powder is shipped under about 50% water for safety. Excess water is decanted off prior to use, but the powder cannot be dried prior to use because it would ignite. Hence, it is added to the charge while wet. The water content of the wet powder will vary according to how long the powder has had an opportunity to settle, how well it was drained and whether it got compacted ("tap" density) during handling. An estimate of water content based on the random packing of spheres might indicate about 35 vol. % water, while measurement taken from depth occupying a jar of A-5000 Sponge Nickel Catalyst indicates that 32 vol. % might be reasonable. The range for low porosity, well packed spheres of optimal diameter may be as low as about 20 vol %, while the maximum, is less than, 50 vol. % water, for which supernatant is always present, say 40 vol% water. The density of nickel is about 8.9 times that of water so 20 vol. % water would be about 2.7 wt. % water and 40 vol. % would be about 7 wt. % water and 35 vol. % water would be about 5.7 wt. % and 32 vol. % would be about 5 wt. % water. Therefore, a likely range in water content of the catalyst as added to the charge would be about 3 to about 7 wt. %, with about 5 wt. % most likely. The process of the prior art used about 2.0 wt. % to about 2.44 wt. % Raney catalyst, therefore about 0.06 to about 0.17 wt. %, and probably about 0.11 wt. % total water was added to the charge from this source, which was removed by the drying step. The improved process of the present invention may be done with about 15 wt. % less catalyst than the prior art if desired, and so about 1.7 to about 2.1 wt. % catalyst is used, contributing from about 0.05 to about 0.15 wt. % water, more probably about 0.10 wt. %, water to the charge.

The Alkali Metal Hydroxide

About 50 wt. % sodium hydroxide solution is preferred due to cost and availability, but 45 wt. % KOH solution may be used as well as aqueous lithium hydroxide. For industrial use, the aqueous form provides ease of meter, mix, dispense and to avoid needless exotherm from heat of mixing. When 50 wt. % sodium hydroxide is used, it is used at about 8% of the catalyst weight. Therefore, the amount of water introduced by the sodium hydroxide solution will vary from about 0.07 wt. % (0.017×0.5×0.08×100) to about 0.10 wt. % (0.0244×0.5×0.08×100) of the charge. Therefore, the water introduced to the charge by the catalyst and aqueous hydroxide combined will range from about 0.1 wt. % to about 0.3 wt. %, and most likely be about 0.2%. This compares to about 0.8% for the prior art industrial process.

The reaction conditions of this invention, time, temperature and pressure, are to a large extent interchangeable, as will be recognized by the skilled practitioner. Shorter reaction times may be had at higher temperatures, as is understood through the Arrhenius relationship, but individual characteristics of reactors, like materials and strength of construction, Watts of heat available for the mass of the charge, thermal insulation losses, temperature control to reduce reaction rate and the like all contribute to practical decisions of what temperature is desirable. These equivalencies should be kept in mind when considering the preferred reaction conditions presented below, which are used in the bench experiments to simulate an existing unique industrial scale autoclave reactor, as opposed to being a search for greenfield optimal conditions.

The Temperature

The temperature should be at least about 150°0C., but about 160° C. is preferred and the temperature can go to about 220° C., if the equipment allows. Note that it is sometimes desirable to increase the hydrogen pressure prior to reaching final temperature, say from about 300 psi to about 400 psi at about 121° C.

The Hydrogen Pressure

The hydrogen pressure should be at least about 250 psi, but about 300 psi is more preferred and about 400 psi is most preferred and the pressure can go to as high as the equipment allows, which for some autoclaves is as high as about 2500 psi.

The Reaction Time The reaction time should be at least 2 hours to get meaningful conversion, but 3 hours is more preferred for product with acceptable amine values and about 4 hours is most preferred.

Examples 1 and 2 are an attempt to simulate the industrial autoclave prior art process on a laboratory scale. The process involves charging the reagents, drying them under vacuum, cooling the mixture, back adding water and finishing the reaction. Example 3 introduces the elimination of the drying and water addition steps. Example 4 is a comparison of the improved process to the prior art process on an industrial (1000 kg) scale as opposed to the lab (kg) scale of Examples 1, 2 and 3, to make sure that the reaction would work on a large scale. Example 5 uses partially pre-hydrogenated dimer dinitrile as a starting material.

The following examples will serve to further illustrate the invention, but should not be construed to limit the invention, unless expressly set forth in the appended claims. The reactants and other specific ingredients are presented as being typical, and various modifications can be derived in view of the foregoing disclosure within the scope of the invention. All parts, percentages, and ratios are by weight unless otherwise indicated in context.

EXAMPLES

Example 1

In order to simulate the aforementioned prior art autoclave process for possible cycle time improvements, a reaction was run based on that procedure. The equipment used was a 500 ml. 3-neck flask equipped with a mechanized stirrer, Claissen head with vacuum take off, heating mantel, pot thermometer. The reagents used were 300.22 g (300 g theoretical) dimer dinitrile #513, 7.50 g (7.33 g theoretical) A-5000 Sponge Nickel Catalyst (Activated Metals & Chemicals, Inc., Seiverville, Tenn.), 0.67 g (0.59 g theoretical) sodium hydroxide 50% in $H_2O$ and 2.3 g (2.2 g theoretical) water. The nitrile, catalyst, and caustic solution were charged to the flask.

| Time | Pot Temp (°C.) | Vacuum ("Hg) | |
|---|---|---|---|
| 9:15 | 22 | — | Heat, Stirrer, Vacuum on |
| 9:30 | 57 | 24.5 | |
| 9:45 | 89 | 25.0 | |
| 10:35 | 130 | 25.5 | |
| 10:50 | 130 | 25.5 | Heat off |
| 12:45 | 35 | | |

The material was transferred to a 600 ml. Parr Autoclave, the water added, and the hydrogenation run.

| Time | Temp. (°C.) | Press. (psi $H_2$) | |
|---|---|---|---|
| 1:05 | 36 | — | Stirrer → Heat on |
| 1:10 | 102 | → 400 PSI | |
| 1:20 | 177 | 50 → 400 | |
| 1:30 | 167 | 70 → 400 | |
| 1:45 | 159 | 150 → 400 | |
| 2:00 | 160 | 100 → 400 | |
| 2:15 | 160 | 100 → 400 | |
| 2:30 | 160 | 180 → 400 | |
| 2:45 | 159 | 160 → 400 | |
| 3:00 | 160 | 200 → 400 | |
| 3:15 | 160 | 200 → 400 | |
| 3:40 | 160 | 250 | Cooling on, Heat off |

After cooling the mixture was filtered through Perlite 476 (made by Grefco); 271.1 g was recovered. Analysis of the product showed 80% primary amine and 20% nitrile, no secondary or tertiary amines were seen with C-13→APT NMR (nuclear magnetic resonance) and confirmed by IR (infrared spectrophotometry). Based on these results, the reaction was repeated, see Example 2 below, to get a higher conversion by hydrogenating the organic nitrile longer than the 2 hours and 20 minutes used in this example.

Example 2

Since there was still ca. 20% nitrile remaining in the product of Example 1, the test was repeated for a longer time. The equipment used was the same as used in Example 1 except a magnetic stirrer was used in place of the mechanical stirrer. The reagents used were 300.1 g dimer dinitrile #513, 7.8 g A-5000 Sponge Nickel Catalyst, 0.8 g sodium hydroxide 50% in $H_2O$ and 2.2 distilled water. The nitrile, catalyst, and sodium hydroxide solution were charged to the flask.

| Time | Pot. Temp (°C.) | Vacuum ("Hg) | |
|---|---|---|---|
| 9:00 | 19 | — | Heat and Vacuum on |
| 9:15 | 51 | 26 | |
| 9:30 | 73 | 26 | |
| 9:50 | 104 | 26 | |
| 10:10 | 135 | 26 | Heat off |
| 10:30 | 100 | 26 | Vacuum off. |

The material was transferred to a 600 ml. autoclave, the water was added and the mixture was hydrogenated.

| Time | Temp. (°C.) | Press. (psi $H_2$) | |
|---|---|---|---|
| 10:45 | 43 | — | Heat on |
| 11:00 | 119 | → 400 | |
| 11:01 | 172 | 400 | |
| 11:45 | 159 | 400 | |
| 12:02 | 160 | 400 | |
| 12:24 | 160 | 400 | |
| 12:36 | 160 | 400 | |
| 12:52 | 160 | 400 | |
| 1:08 | 160 | 410 | |
| 1:26 | 160 | 390 → 400 | |
| 1:48 | 160 | 390 → 400 | |
| 2:04 | 159 | 400 | Sampled |
| 2:20 | 160 | 390 → 400 | |
| 2:33 | 160 | 400 | |
| 3:01 | 160 | 400 | Cooling |

The 2:04 sample, which was at temperature for 3 hours and 4 minutes, and product, which was at temperature for 4 hours, were filtered through Perlite 476; the weight of the final product was 230 g. IR analysis showed the 2:04 cut to have ca. 5% nitrile remaining and the final product had ca. 1% nitrile. The amine value for the final product averaged 190.2, while that of the 2:04 cut averaged 185.0. Both samples meet the 185 minimum specification. Subsequent hydrogenation examples are run at 4 hours.

Example 3

Dimer diamine was prepared without the drying and back adding water steps. The equipment used was the same as the autoclave used in the previous example. The reagents used were 300.1 g dimer dinitrile #513, 8.1 g A-5000 Sponge Nickel Catalyst and 0.8 g sodium hydroxide 50% in water. The reagents were charged to the autoclave and hydrogenated.

| Time | Temp. (°C.) | Press. (psi $H_2$) | |
|---|---|---|---|
| 10:00 | 18 | — | Heat and Stirrer on |
| 10:10 | 136 | → 300 | |
| 10:15 | 166 | 100 → 300 | |
| 10:18 | 173 | 200 → 300 | |
| 10:20 | 171 | 200 → 300 | |
| 10:25 | 167 | 200 → 300 | |
| 10:30 | 160 | 100 → 300 | |
| 10:45 | 160 | 100 → 300 | |
| 10:50 | 160 | 100 → 300 | |
| 11:35 | 159 | 250 → 300 | |
| 11:45 | 160 | 190 → 300 | |
| 12:15 | 160 | 280 → 300 | |
| 12:45 | 160 | 280 → 300 | |
| 1:15 | 160 | 300 | |
| 2:15 | 160 | 300 | Heat off |

The material was cooled and then filtered through Perlite 476. The dimer diamine product weighed 270.7 g and had an amine value of 189.9 and a Gardner color of 9.0. IR showed no nitrile and a very small amount of amide. The moisture content averaged 0.71 wt. %.

Analysis by IR of the above material and the prior art sample showed that the only apparent difference was a small peak at 1670- cm. This could be due to a very small amount of carbonate present. NMR results agreed with the above IR results. The secondary amine is slightly higher in the lab sample but within specification.

Example 4

Twenty-six ca. 4,200 kg batches of dimer diamine were produced in the industrial autoclave. Four of these runs were done using the improved process steps and low water content of Example 3 and the rest done as in the prior art Example 2, and both used the temperature, time and pressure parameters of Examples 2 and 3. One of the prior art runs was removed from consideration since it had to be re-hydrogenated and one of the new procedure batches was disregarded since it "ran away" (uncontrolled exotherm). The successful results from the prior art runs were compared to the improved process runs:

| TEST | Prior Art | Improved Process |
| --- | --- | --- |
| Total Amine Value | 194.9 | 195.3 |
| II & III Amine Value | 3.45 | 3.83 |

All improved process lots met specification. The observation was made that the improved process was a "hotter" procedure and provides the opportunity to reduce catalyst loading. This is now done by increasing the dimer dinitrile charge by about 10 to about 15%. When the resulting primary dimer diamine is distilled, typical properties are an amine value of about 200 to about 210, an iodine value from about 80 to about 120, a specific gravity of about 0.84 to about 0.92, a viscosity of about 173 cps and a combining weight of about 282.

Example 5

Dimer dinitrile #523 is used as a precursor and processed as in Example 4 to make dimer diamine. Typical properties after distillation are an amine value of about 200 to about 210 and an iodine value from about 5 to about 20, a specific gravity of about 0.84 to about 0.92, a viscosity of about 257 cps and a combining weight of about 280.

A new procedure for the production of primary amines, particularly dimer diamines, has been developed and shown to be viable. The main advantage of this new procedure is to reduce cycle time by eliminating the drying and water back adding steps from the current procedure. The new procedure also has the potential of allowing reduced catalyst loadings or increased nitrile charge and shorter cycle time and reduced energy consumption.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a process for the catalytic hydrogenation of at least one organic nitrile to at least one primary amine comprising the following steps:

charging an organic nitrile to an autoclave;

removing oxygen from the organic nitrile;

adding Raney catalyst slurry and aqueous alkali metal hydroxide under an inert gas blanket, wherein the Raney nickel catalyst slurry and aqueous alkali metal hydroxide contribute from about 0.1 to about 0.3% water;

drying the charge in the autoclave;

adding water to the autoclave charge;

pressurizing with hydrogen;

heating the converter toward a final temperature greater than about 110° C.;

controlling the reaction exotherm that occurs as the organic nitrile is reduced to a primary amine;

cooling the resulting primary amine when the reaction is complete; and separating the amine from the catalyst to obtain the desired primary amine product, wherein the improvement comprises eliminating the steps of:

drying the charge in the autoclave; and adding water to the autoclave charge, whereby cycle time and energy use are both reduced.

2. The process of claim 1, wherein the process further comprises the step of cooling the autoclave to below the boiling point of water and the improvement further comprises eliminating the step of cooling the converter to below the boiling point of water.

3. In the process of claim 1, wherein the organic nitrile is substantially dimer dinitrile.

4. The process of claim 1, wherein the organic nitrile is selected from the group consisting of acrylonitrile, methacrylonitrile, propionitrile, benzonitrile, 2-methylglutaronitrile, isobutyronitrile, dicyanocyclooctane, nitrilotriacetonitrile, isophthalonitrile, terephthalonitrile, 1,3,5-tricyanobenzene, o-, m-, and p-toluinitrile, o-, m-, and p-aminobenzonitrile, phthalonitrile, trimesonitrile, 1-naphthonitrile, 2-naphthonitrile, cyclobutanecarbonitrile, cyclopentanecarbonitrile, cyclohexanecarbonitrile, 1,4-cyclohexanedicarbonitrile, 1,2,4,5-cyclohexanetetracarbonitrile, cycloheptanecarbonitrile, 3-methylcycloheptanecarbonitrile, cyclooctanecarbonitrile, butyronitrile, valeronitrile, capronitrile. 2,2-dimethylpropanenitrile, enanthonitrile, caprylnitrile, pelargonitrile, decanenitrile, hendecanenitrile, lauronitrile, tridecanenitrile, myristonitrile, pentadecanenitrile, palmitonitrile, heptadecanenitrile, stearonitrile, phenylacetonitrile, malononitrile, succinonitrile, glutaronitrile, adiponitrile, 1,3,5-tricyanopentane, 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3- methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile 2,4,8,10-tetrapropyl-6-methylenedodecanedinitrile, 2,26-dimethyl-14-methyleneheptacosanedinitrile, aminoacetonitrile, hexamethylene-1,6-dinitrile, the cyanoethylated derivatives of methanol, ethanol, butanol, pentanol, methyl amine, ethyl amine, butyl amine, octyl amine, ethylene glycol, propylene glycol, butylene glycol, propylene glycol, diethylene glycol, dipropylene glycol, hydroquinone, phloroglucinol, 1,4-cyclohexanediol, 1,4-di(hydroxymethyl)cyclohexane, polyethylene glycols, polypropylene glycols, polyoxyalkylene polyethers, polyester polyols, polyol adducts derived from ethylene and propylene oxide and methylenedianiline and polyethylene polyphenylamine mixtures, vinyl reinforced polyether polyols, polyols obtained by the polymerization of styrene or acrylonitrile in the presence of the polyether, polyacetals, polycarbonate polyols, resole polyols, hydroxy terminated polybutadiene resins, ethylene diamine, butylene diamine, polyamines, primary amine terminated polyether resins, $C_{12}H_{25}CN$, $NC—(CH_2)_6—CN$, $NC—(CH_2)_{18}—CN$, $CH_3CH_2CH_2—O—CH_2CH_2—CN$, $NC—CH_2CH_2CH_2—O—CH_2CH_2—O—CH_2CH_2CH_2—CN$, $NCCH_2CH_2OCH_2CH_2CH_2OCH_2CH_2CN$, $NCCH_2CH_2OCH_2CH(CH_3)OCH_2CH_2CN$, $NCCH_2CH_2O(CH_2)_4OCH_2CH_2CN$, $NCCH_2CH_2OCH_2CH_2CH(CH_3)OCH_2CH_2CN$, $[NCCH_2CH_2OCH(CH_3)-]_2$, $(CH_3)_2C(OCH_2CH_2CN)CH_2OCH_2CH_2CN$, $NCCH_2CH_2O(CH_2)_3CH(CH_3OCH_2CH_2CN$, $NCCH_2CH_2O(CH_2)_5OCH_2CH_2CN$, $NCCH_2CH_2O(CH_2)_6OCH_2CH_2CN$, $NCCH_2CH_2O(CH_2)_{10}OCH_2CH_2CN$, $NC—CH_2CH_2NH(CH_2)_{12}NHCH_2CH_2—CN$, 3,3'-(ethylenedioxy)-dipropionitrile ($NC—C_2H_4—O—C_2H_4—O—C_2H_4—CN$) and mixtures thereof.

5. The process of claim 1, wherein the organic nitrile is selected from the group consisting of aliphatic nitrites, aromatic nitrites, cycloaliphatic nitrites, heterocyclic nitrites heteroaliphatic nitrites and mixtures thereof.

6. In a process for the hydrogenation of organic nitrites into primary amines, which consists of contacting at least one organic nitrile, about 0.1 part alkali metal hydroxide, at least one Raney nickel hydrogenation catalyst, 1 to 2 wt. % water for 110 minutes reaction time at 140° C. and 200 psi hydrogen pressure, wherein the improvement comprises decreasing the water to about 0.1% to about 0.6 wt. %.

7. In the process of claim 6, wherein the organic nitrile is substantially dimer dinitrile.

8. The process of claim 6, wherein the organic nitrile is selected from the group consisting of acrylonitrile, methacrylonitrile, propionitrile, benzonitrile, 2-methylglutaronitrile, isobutyronitrile, dicyanocyclooctane, nitrilotriacetonitrile, isophthalonitrile, terephthalonitrile, 1,3,5-tricyanobenzene, o-, m-, and p-tolunitrile, o-, m-, and p-aminobenzonitrile, phthalonitrile, trimesonitrile, 1-naphthonitrile, 2-naphthonitrile, cyclobutanecarbonitrile, cyclopentanecarbonitrile, cyclohexanecarbonitrile, 1,4-cyclohexanedicarbonitrile, 1,2,4,5-cyclohexanetetracarbonitrile, cycloheptanecarbonitrile, 3-methylcycloheptanecarbonitrile, cyclooctanecarbonitrile, butyronitrile, valeronitrile, capronitrile, 2,2-dimethylpropanenitrile, enanthonitrile, caprylnitrile, pelargonitrile, decanenitrile, hendecanenitrile, lauronitrile, tridecanenitrile, myristonitrile, pentadecanenitrile, palmitonitrile, heptadecanenitrile, stearonitrile, phenylacetonitrile, malononitrile, succinonitrile, glutaronitrile, adiponitrile, 1,3,5-tricyanopentane, 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile 2,4,8,10-tetrapropyl-6-methylenedodecanedinitrile, 2,26-dimethyl-14-methyleneheptacosanedinitrile, aminoacetonitrile, hexamethylene-1,6-dinitrile, the cyanoethylated derivatives of methanol, ethanol, butanol, pentanol, methyl amine, ethyl amine, butyl amine, octyl amine, ethylene glycol, propylene glycol, butylene glycol, propylene glycol, diethylene glycol, dipropylene glycol, hydroquinone, phloroglucinol, 1,4-cyclohexanediol, 1,4-di(hydroxymethyl)cyclohexane, polyethylene glycols, polypropylene glycols, polyoxyalkylene polyethers, polyester polyols, polyol adducts derived from ethylene and propylene oxide and methylenedianiline and polyethylene polyphenylamine mixtures, vinyl reinforced polyether polyols, polyols obtained by the polymerization of styrene or acrylonitrile in the presence of the polyether, polyacetals, polycarbonate polyols, resole polyols, hydroxy terminated polybutadiene resins, ethylene diamine, butylene diamine, polyamines, primary amine terminated polyether resins, $C_{12}H_{25}CN$, $NC—(CH_2)_6—CN$, $NC—(CH_2)_{18}—CN$, $CH_3CH_2CH_2—O—CH_2CH_2CN$, $NC—CH_2CH_2CH_2—O—CH_2CH_2—O—CH_2CH_2CH_2—CN$, $NCCH_2CH_2OCH_2CH_2CH_2OCH_2CH_2CN$, $NCCH_2CH_2OCH_2CH(CH_3)OCH_2CH_2CN$, $NCCH_2CH_2O(CH_2)_4OCH_2CH_2CN$, $NCCH_2CH_2OCH_2CH_2CH(CH_3)OCH_2CH_2CN$, $[NCCH_2CH_2OCH(CH_3)-]_2$, $(CH_3)_2C(OCH_2CH_2CN)CH_2OCH_2CH_2CN$, $NCCH_2CH_2O(CH_2)_3CH(CH_3) OCH_2CH_2CN$, $NCCH_2CH_2O(CH_2)_5OCH_2CH_2CN$, $NCCH_2CH_2O(CH_2)_6OCH_2CH_2CN$, $NCCH_2CH_2O(CH_2)_{10}OCH_2CH_2CN$, $NC—CH_2CH_2NH(CH_2)_{12}NHCH_2CH_2—CN$, 3,3'-(ethylenedioxy)-dipropionitrile ($NC—C_2H_4—O—C_2H_4—O—C_2H_4—CN$) and mixtures thereof.

9. The process of claim 6, wherein the organic nitrile is selected from the group consisting of aliphatic nitrites, aromatic nitrites, cycloaliphatic nitrites, heterocyclic nitrites, heteroaliphatic nitriles and mixtures thereof.

10. The process of claim 6, wherein the improvement comprises decreasing the water to about 0.1% to about 0.4 wt. %.

11. The process of claim 6, wherein the improvement comprises decreasing the water to about 0.1% to about 0.3 wt. %.

12. The process of claim 6, wherein the improvement comprises decreasing the water to about 0.2%.

13. The process of claim 6, wherein the improvement further comprises increasing the temperature to at least about 150° C. to about 220° C.

14. The process of claim 6, wherein the improvement further comprises increasing the temperature to about 160° C.

15. The process of claim 6, wherein the improvement further comprises increasing the pressure to at least about 250 psi to about 2,500 psi.

16. The process of claim 6, wherein the improvement further comprises increasing the pressure to at least about 300 psi to about 400 psi.

17. The process of claim 6, wherein the improvement further comprises increasing the reaction time to at least about 2 hours.

18. The process of claim 6, wherein the improvement further comprises increasing the reaction time to about 3 hours.

19. The process of claim 6, wherein the improvement further comprises increasing the reaction time to about 4 hours.

* * * * *